United States Patent [19]

Hartmann et al.

[11] 4,399,001
[45] Aug. 16, 1983

[54] SEPARATING OFF ORGANIC IODINE COMPOUNDS FROM ACETALDEHYDE-FREE CARBONYLATION PRODUCTS OF METHANOL, METHYL ACETATE AND DIMETHYL ETHER

[75] Inventors: Horst Hartmann, Boehl-Iggelheim; Waldhelm Hochstein, Freinsheim; Gerd Kaibel, Lampertheim; Franz-Josef Mueller, Wachenheim, all of Fed. Rep. of Germany

[73] Assignee: BASF Aktiengesellschaft, Ludwigshafen, Fed. Rep. of Germany

[21] Appl. No.: 315,726

[22] Filed: Oct. 28, 1981

[30] Foreign Application Priority Data

Nov. 29, 1980 [DE] Fed. Rep. of Germany ....... 3045081

[51] Int. Cl.$^3$ .............................................. B01D 3/36
[52] U.S. Cl. .................................... 203/70; 568/492
[58] Field of Search ............... 568/492, 913; 560/232, 560/248; 562/519, 608; 570/262; 203/69, 70, 68

[56] References Cited

U.S. PATENT DOCUMENTS 2,452,797 11/1948 Smith ................................... 203/70

Primary Examiner—Frank Sever
Attorney, Agent, or Firm—John H. Shurtleff

[57] ABSTRACT

A process for separating off organic iodine compounds from acetaldehyde-free carbonylation products of methanol, methyl acetate and dimethyl ether by removing the iodine compounds by azeotropic distillation with a hydrocarbon having a boiling point, under atmospheric pressure, of 25-55° C.

8 Claims, No Drawings

SEPARATING OFF ORGANIC IODINE COMPOUNDS FROM ACETALDEHYDE-FREE CARBONYLATION PRODUCTS OF METHANOL, METHYL ACETATE AND DIMETHYL ETHER

The present invention relates to a novel process for separating off organic iodine compounds, in particular methyl iodide, from acetaldehyde-free carbonylation products of methanol, methyl acetate and dimethyl ether.

It is generally known that methanol, methyl acetate and dimethyl ether can react in many ways with carbon monoxide or with carbon monoxide and hydrogen in the presence of carbonyl-forming metal, chiefly those of group VIII of the periodic table of the elements, to give various products.

These reactions are usually grouped under the heading carbonylation and specifically include, inter alia:

carbonylation (in the narrower sense) of methanol or dimethyl ether using, inter alia, Co, Ni or Rh catalysts, to give mixtures which essentially consist of methanol, acetic acid and methyl acetate, carbonylation (in the narrower sense) of methyl acetate using, inter alia, Co, Ni or Rh catalysts, to give mixtures which essentially consist of methyl acetate and acetic anhydride.

homologization of methanol and dimethyl ether with $CO/H_2$ in the presence of, inter alia, Co, Ni or Rh catalysts, to give mixtures which in addition to methanol, essentially contain acetaldehyde, ethanol, methyl acetate, acetaldehyde dimetnyl acetal and water, depending on the reaction conditions, and homologization of methyl acetate with $CO/H_2$ in the presence of, inter alia, Co, Ni or Rh catalysts, to give mixtures which essentially consist of ethylidene diacetate, vinyl acetate, methyl acetate, ethyl acetate, water and methanol, depending on the reaction conditions.

Numerous embodiments of all of these processes are known or conceivable, so that a corresponding number of reaction mixtures of different qualitative and quantitative compositions are obtained. However, most embodiments of these carbonylation reactions have the common feature that they are carried out in the presence of iodides, so that the reaction mixtures always contain appreciable amounts of organo-iodine compounds, in particular, methyl iodide.

These organo-iodine compounds are extremely difficult to separate from the remaining organic components of the carbonylation mixtures.

Fractionation, if possible at all in spite of the many azeotropes which can be formed, requires uneconomically high expenditure on separation, and chemical methods, such as oxidation, reduction or treatment with alkali, are not feasible because of the sensitivity of some carbonylation products, quite apart from the fact that these methods are technologically cumbersome and usually only replace a difficult separation problem by others which are less difficult in principle.

According to German Laid-Open Application DOS No. 2,940,751, for example, methyl iodide is removed from carbonylation products of methyl acetate by reaction with alkali metal acetates, alkali metal iodides being obtained. However, since this reaction only takes place at elevated temperatures, it must be carried out under superatmospheric pressure and the iodine salts must then be separated off. These measures and the subsequent recycling of the iodides to the process are, however, technologically involved and unsatisfactory, and, in particular, they cannot be harmoniously incorporated into a continuous process sequence. Finally, if water is present as a component of the reaction mixture, it is virtually impossible to remove iodine by the above method.

It is an object of the present invention to remove methyl iodide and other organic iodine compounds from reaction mixtures obtained in the carbonylation of methanol, methyl acetate and dimethyl ether, in a simpler and more economic manner than hitherto.

We have found that this object is achieved and that methyl iodide and other organic iodine compounds can be elegantly separated off from acetaldehyde-free reaction mixtures resulting from the carbonylation of methanol, methyl acetate and dimethyl ether if the iodine compounds are removed by azeotropic distillation with a hydrocarbon having a boiling point, under atmospheric pressure, of 25°–55° C.

Surprisingly, the process according to the invention can be used not only with certain carbonylation products of methanol, methyl acetate and dimethyl ether, but also with any mixtures obtained in these reactions. Further working up of such mixtures thus no longer involves the problem of removal of iodine, and can therefore be carried out in any desired manner.

If the mixtures contain acetaldehyde, this is separated off beforehand, together with a portion of the iodine compounds, and is advantageously subjected to the purification process of our German Patent No. 3,045,105 (corresponding to our U.S. application, Ser. No. 316,301, filed Oct. 29, 1981, now pending) by azeotropic distillation with the hydrocarbons which are used in the present case and likewise from azeotropes or azeotrope-like mixtures with acetaldehyde.

The acetaldehyde is washed out of these azeotropes or azeotrope-like mixtures with water, after which the hydrocarbons are recycled back to the azeotropic distillation.

About 10–200 g of the hydrocarbon are used per gram of iodine compounds, chiefly methyl iodide, for the azeotropic distillation, according to the invention, of the acetaldehyde-free carbonylation products or of mixtures thereof. The preferred hydrocarbon is isopentane (2-methylbutane), and n-pentane, cyclopentane and 2,2-dimethyl butane are also suitable.

Separation of the mixtures consisting of the iodine compounds and the hydrocarbons from the carbonylation products presents no problems and generally requires only a column, of any desired construction, and having about 20–40 theoretical plates. The azeotropes have boiling points of 25°–50° C., that is to say below that of methyl acetate, which is the component with the lowest boiling point in the liquid reaction product. If the iodine-containing azeotropes are recycled to the synthesis stage, they do not have to be condensed so that it is generally advisable to carry out the reaction under atmospheric pressure. On the other hand, if the azeotropes are to be condensed, it is advantageous to carry out the reaction under a pressure of about 1.5–3 bar to enable the cooling to be carried out with water at room temperature.

The iodine can be removed from the iodine-containing mixtures, in which the concentration of iodine compounds is about 0.5–2% by weight or more, by any chemical route, for example by treatment with alkali metals or alkali metal hydroxide solutions and subsequent separation of the iodides from the inert hydrocarbons. However, it is particularly advantageous to recycle the iodine-containing hydrocarbons directly to the carbonylation reaction stage. A closed circulation system both of the iodine and of the hydrocarbons is thus formed.

The process according to the invention is in principle independent of the conditions and purpose of the carbonylation reaction, provided only that iodine compounds have been used as activators in the carbonylation catalyst system, as is the case in most of the syntheses of this type carried out industrially. There is therefore no need to list in detail the various reaction conditions for the above embodiments of carbonylation reactions.

The process according to the invention enables the iodine content of carbonylation products or of mixtures thereof to be lowered from about 1000–10,000 ppm to 0.1–2 ppm in an extremely simple manner.

EXAMPLE

Isopentane was added to various model mixtures which contained methyl iodide and in which the nature and amount of the components approximately corresponded to carbonylation mixtures, and the mixtures were then continuously separated, in a packed column having about 28 theoretical plates, and using a reflux ratio r, into an isopentane top fraction, and a bottom fraction, the composition of which corresponded to that of the original mixture, in all but the methyl iodide content.

The methyl iodide content of each of the two fractions was determined by gas chromatography.

The table shows the conditions and results of the individual experiments.

TABLE

| Experiment No. | Starting material or mixture (feed) g/h | Isopentane g/h | r | Methyl iodide content [ppm] Feed | Methyl iodide content [ppm] Bottom fraction |
|---|---|---|---|---|---|
| 1 | 180 of acetic acid | 55 | 0.5 | 4000 | 1–2 |
| 2 | 100 of acetic acid 100 of methyl acetate | 57 | 1.0 | 5000 | 0.1 |
| 3 | 95 of acetic anhydride 95 of methyl acetate | 60 | 1.0 | 5000 | 0.1–0.8 |
| 4 | 57 of acetic anhydride | 55 | 1.0 | 7000 | 0.1 |
| 5 | 57 of methyl acetate 57 of ethylidene diacetate 50 of acetic anhydride 50 of ethylidene diacetate 50 of vinyl acetate 50 of acetic acid | 37 | 1.0 | 1000 | 1 |
| 6 | 67 of acetic anhydride 67 of ethylidene diacetate 67 of methyl acetate | 44 | 1.0 | 2000 | 1 |

We claim:
1. A process for separating off organic iodine compounds as an impurity from acetaldehyde-free carbonylation products of methanol, methyl acetate and dimethyl ether, which process comprises:
   removing the organic iodine impurity by azeotropic distillation of the acetaldehyde-free carbonylation product with a hydrocarbon having a boiling point, under atmospheric pressure, of 25°–50° C., said distillation being carried out under conditions of temperature and pressure sufficient to obtain substantially all of the organic iodine impurity in the azeotrope distillate fraction and to obtain the remaining carbonylation products in one or more higher boiling fractions.
2. A process as claimed in claim 1, wherein isopentane is used as the hydrocarbon.
3. A process as claimed in claim 2, wherein the chief impurity to be removed is methyl iodide.
4. A process as claimed in claim 1, wherein the azeotropic distillation of the acetaldehyde-free carbonylation product is carried out at a pressure of about 1.5–3 bar.
5. A process as claimed in claim 1, wherein the hydrocarbon is used in an amount of about 10–200 grams per gram of the organic iodine impurity.
6. A process as claimed in claim 1, wherein the hydrocarbon is selected from the class consisting of isopentane, n-pentane, cyclopentane and 2,2-dimethylbutane.
7. A process as claimed in claim 5, wherein the hydrocarbon is isopentane.
8. A process as claimed in claim 1, wherein the chief impurity to be removed is methyl iodide.

* * * * *